United States Patent [19]

Lombardino et al.

[11] 4,268,516
[45] May 19, 1981

[54] [1]BENZOTHIOPYRANO[4,3-C]PYRAZOLES AS IMMUNOREGULATORY AGENTS

[75] Inventors: Joseph G. Lombardino, Niantic; Ivan G. Otterness, Ledyard, both of Conn.; James F. Muren, Lee's Summit, Mo.

[73] Assignee: Pfizer Inc., New York, N.Y.

[21] Appl. No.: 133,652

[22] Filed: Mar. 24, 1980

Related U.S. Application Data

[63] Continuation-in-part of Ser. No. 950,386, Oct. 11, 1978, abandoned.

[51] Int. Cl.³ .............. A61K 31/415; C07D 495/04; C07D 487/00
[52] U.S. Cl. .................. 424/273 P; 548/359
[58] Field of Search .................. 548/359, 370; 424/273 P

[56] References Cited

U.S. PATENT DOCUMENTS

| | | | |
|---|---|---|---|
| 3,235,564 | 2/1966 | Wagner | 548/370 |
| 3,816,438 | 6/1974 | Houlihan | 548/370 |
| 3,932,434 | 1/1976 | Paget | 424/270 |

OTHER PUBLICATIONS

McCarty, Arthritis and Allied Conditions, pp. 375-390, Lea & Febiger, Philadelphia, 1979.
Pagani et al, Chem. Abst. 1971, vol. 75, No. 48829c.
Scrowston et al, J. Chem. Soc. 1976, Perkin Trans., pp. 749-754.
Huskisson et al, Lancet 1976, vol. 1, pp. 393-395.
Runge et al, Arth. and Rheum. 1977, vol. 20, pp. 1445-1448.
Schneller in "Advances in Heterocyclic Chemistry", vol. 18, Karitzky & Boulton, Eds., Academic Press, New York, 1975, pp. 88-94.

Primary Examiner—Henry R. Jiles
Assistant Examiner—Natalia Harkaway
Attorney, Agent, or Firm—Connolly and Hutz

[57] ABSTRACT

1,2,3,4-Tetrahydrobenzothiopyrano[4,3-c]pyrazol-3-ones and 2,3-dihydro[1]benzothiopyrano[4,3-c]pyrazol-3-ones, of respective structure I and II,

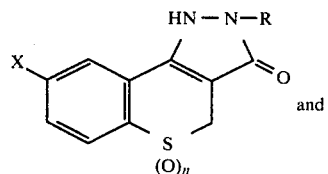

and

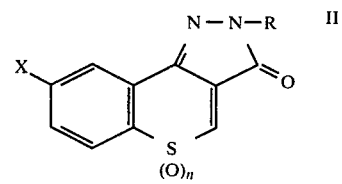

wherein
  n is an integer of value from 0 to 2;
  R is phenyl; phenyl monosubstituted with chloro, bromo, fluoro, methyl, methoxy, nitro or trifluoromethyl; or phenyl disubstituted with chloro; and
  X is hydrogen or chloro;
are described.

These novel compounds are immunoregulators which, through suppression of the immune response in mammals, are useful in inhibiting rejection of organ transplants, as well as in the therapy of auto-immune diseases.

22 Claims, No Drawings

[1]BENZOTHIOPYRANO[4,3-c]PYRAZOLES AS IMMUNOREGULATORY AGENTS

CROSS REFERENCE TO RELATED APPLICATION

This application is a continuation-in-part of application Ser. No. 950,386 filed Oct. 11, 1978 now abandoned.

BACKGROUND OF THE INVENTION

Immunosuppressive agents find current use in two principal clinical circumstances: organ transplantation and auto-immune diseases. The latter are pathological conditions arising from immunological reactions injurious to the body's own constituents. Examples of such conditions include idiopathic thrombocytopenic purpura, auto-immune hemolytic anemia, acute glomerulonephritis, systemic lupus erythematosis, polyarteritis nodosa, rheumatoid arthritis, dermatomyositis, scleroderma and giant-cell arteritis.

The following drugs have been found clinically useful in modifying immunological processes:
1. Alkylating Agents
2-[bis(2-chloroethyl)amino]tetrahydro-2H-1,3,2-oxazaphosphorine-2-oxide (cyclophosphamide)
p-di(2-chloroethyl)amino-L-phenylalanine (melphalan)
2. Purine and Pyrimidine Analogues
6-mercaptopurine
6-thioguanine
5-fluorouracil
5-bromodesoxyuridine
6-(1-methyl-4-nitro-5-imidazolyl)mercaptopurine (azathioprine)
3. Folid Acid Antagonists
4-aminofolic acid
4-amino-10-methylfolic acid
4. Steroids
cortisone
prednisone In addition to the compounds listed above, other compounds have been reported to have immunoregulatory activity. These include levamisole [Huskisson et al., Lancet 1, 393 (1976); Runge et al., Arth. and Rheum. 20, 1445 (1977)] and certain N-2-(6-hydroxybenzothiazolyl)-N'-phenylureas (Paget and Wikel, U.S. Pat. No. 3,932,434).

The compounds of the present invention are novel. However, certain [1]-benzothiopyrano[4,3-c]pyrazoles, lacking the 3-keto and 2-phenyl groups of the compounds of the present invention, are reported to be useful as non-estrogenic antifertility agents (Houlihan, U.S. Pat. No. 3,816,438) or as antibacterial agents (Wagener, U.S. Pat. No. 3,235,564). Other benzothiopyranopyrazoles of no known utility have also been reported in the literature [for review, see Schneller in "Advances in Heterocyclic Chemistry," Vol. 18, Katritzky and Boulton, eds., Academic Press, New York (1975), pp. 88–94]. Exemplary are 1,4-dihydro[1]benzothiopyrano[4,3-c]pyrazole and its 5,5-dioxide [Pagani and Maiorana, Chim. Ind. (Milan) 53, 469 (1971); Chem Abstr. 75, 48829c]; 2,3,3a,4-tetrahydro[1]benzothiopyrano[4,3-c]pyrazole and its tautomer [Pagani and Maiorana, op. cit.]; and 1-phenyl-1,2,3,5-tetrahydro[2-]benzothiopyrano[4,3-c]pyrazol-3-one [Scrowston and Shaw, J. Chem. Soc. Perkin Trans., 749 (1976)]. The last named compound is an isomer of one of the compounds of the present invention.

SUMMARY OF THE INVENTION

This invention is concerned with a compound selected from the group consisting of those of the formulae:

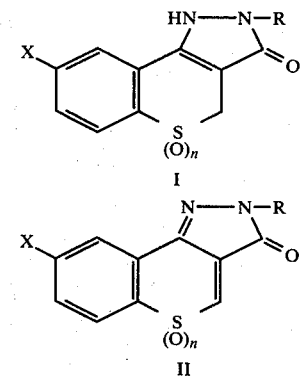

wherein
n is an integer of value from 0 to 2;
R is phenyl; phenyl monosubstituted with chloro, bromo, fluoro, methyl, methoxy, nitro or trifluoromethyl; or phenyl disubstituted with chloro; and
X is hydrogen or chloro.

Compounds of formula I are capable of existing in other tautomeric forms, e.g.,

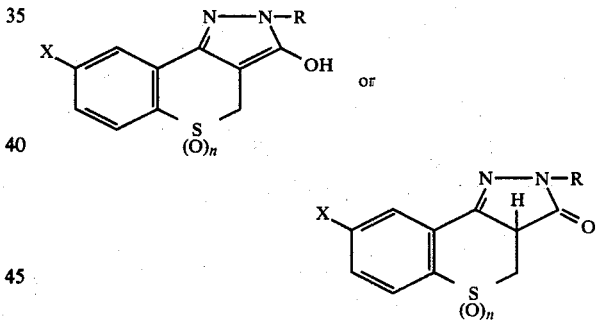

These compounds are capable of suppressing the immune response in mammals and so are useful in inhibiting rejection of organ transplants as well as in the therapy of auto-immune diseases.

The compounds of this invention modify those immune reactions classified as antibody-mediated (humoral) and cell-mediated (cellular) hypersensitivities. The effects on both systems may be shown directly in mice using the El$_4$ tumour cell procedure of Otterness and Chang [Clin. Exp. Immunol., 26, 346–354 (1976)], a procedure which sensitively detects such clinically useful immunosuppressants as cyclophosphamide and azathioprine. This animal test measures the immune-mediated rejection of a tumor allograft (transplant), a process fully analagous in this respect to organ transplant. The effects of these compounds also include inhibition of the secondary migratory arthritic lesions in rats injected with Freund's adjuvant (an induced autoimmune disorder) a procedure reflecting utility in the clinical control of autoimmune diseases.

DETAILED DESCRIPTION OF THE INVENTION

The 1,2,3,4-tetrahydro-[1]benzothiopyrano[4,3-c]pyrazol-3-ones (II, n=0) of this invention are prepared by reacting an ester of the appropriate benzothiopyran carboxylic acid with a slight molar excess of an appropriate hydrazine derivative (free base) in the presence of a small amount of glacial acetic acid under a nitrogen atmosphere. After stirring mechanically to obtain a homogenous mixture, the bath temperature is raised to about 115°–180° C. for about 1 to 35 hours, depending upon temperature, at which time the reaction is substantially complete. The reaction mixture is cooled to room temperature and taken to dryness under vacuum. The residue is triturated with ether and dried. Final purification is accomplished by recrystallization from an appropriate solvent such as isopropanol.

The 1,2,3,4-tetrahydro[1]benzothiopyrano[4,3-c]-pyrazol-3-ones (I, n=1 or 2) are prepared by peroxidation of the simple benzothiopyrans (I, n=0) by the action of 30% hydrogen peroxide. Mild, low-temperature conditions yield the sulfoxides (I, n=1); more vigorous, higher-temperature conditions yield the sulfones (I, n=2).

1,2,3,4-Tetrahydro[1]benzothiopyrano[4,3-c]pyrazol-3-ones (I) of the present invention can be oxidized to the 2,3-dihydro compounds (II) by refluxing for about 30 minutes in a reaction-inert solvent such as benzene in the presence of an oxidant such as chloranil (tetrachloro-p-benzoquinone).

Alternatively, those 2,3-dihydro-[1]-benzothiopyrano[3,4-c]pyrazol-3-ones which are not oxides at sulfur (II, n=0) are obtained by the acid catalyzed dehydration of the corresponding tetrahydro-5-oxide (I, n=1). The latter conversion occurs under relatively mild acidic conditions, e.g. in acetic acid at 85° C. in the presence of a small amount of conc. hydrochloric acid. Under these conditions, the product usually separates directly as a solid on cooling. Alternatively, the acetic acid can be removed by evaporation in vacuo or freeze drying.

The hydrazines required as starting materials for these syntheses are available commercially or are known in the literature. Hydrazines obtained in the form of acid addition salts are converted to the free hydrazines by partitioning the salts between aqueous hydroxide and ether, or other suitable organic solvent, drying the organic extract and then removing the solvent under reduced pressure. This process is generally carried out immediately before use of the hydrazine free base. The 4-oxo-thiochroman-3-carboxylic acid esters required as starting materials are available in the literature, or prepared as detailed in the specific examples below.

Assessment of the immunosuppressant activity was determined in animals.

Assessment in mice was based upon inhibition of the cellular and humoral immune response to El$_4$ tumor cells according to the procedure of Otterness and Chang [Clin. Exp. Immunol. 26, 346 (1976)]. The cellular response as indicated by target cell destruction by sensitized lymphocytes, was measured by a modification of the procedures described by T. G. Canty in J. Nat. Cancer Inst., 45, 761 (1970) and humoral immunity was measured as described by A. R. Sanderson, Nature 204, 250 (1964). Currently known immunosuppressive therapeutic agents are also detected by this procedure [Otterness and Chang, op. cit.].

Groups of 10 BALB/c mice were immunized by intraperitoneal injection with $10^7$ cells from the ascites tumor El$_4$. The tumor was maintained by passage in syngeneic adult C57BL mice. Drug was administered orally dissolved in water with the addition of a small amount of sodium hydroxide to permit solution (circa pH 8.5). Drug treated groups were dosed once daily for nine days. On the tenth day both control (saline treated) and drug treated groups were assayed for the development of humoral and cellular immunity against El$_4$ cells.

The cellular (cell-mediated) immune response was measured as the lysis of El$_4$ cells by the spleen cells of the sensitized mice as described by Otterness and Chang [op. cit.]. Spleens were minced, ground in a mortar and pestle, filtered, washed twice in Hank's minimal essential medium and resuspended to a concentration of $1.5 \times 10^7$ cells/0.5 ml. A mixture of 0.5 ml. of spleen cells and 0.5 ml. of labeled El$_4$ cells ($5 \times 10^4$) was incubated in a $35 \times 110$ mm petri dish for 3 hours at 37° C. in 10% $CO_2$ atmosphere on a rocker platform at 8 reciprocations/minute. The cells were collected and centrifuged, the radioactivity in the supernatant and pellet counted in a gamma counter (Nuclear of Chicago Model #4230), and the percentage lysis determined after correction for lysis of El$_4$ cells in the absence of sensitized spleen cells. Drug effects are recorded as percent inhibition of the control lysis.

Humoral (antibody) immunity was measured using complement dependent lysis of $^{51}Cr$ labeled El$_4$ cells as described previously [Otterness and Chang, op. cit.]. Cells ($1 \times 10^7$) were labeled with 60 microC of $^{51}Cr$ in 10% $CO_2$ for 30 minutes at 37° C., then the labeled cells were washed twice with 45 ml. of cold Hank's minimum essential media. Antibody-dependent lysis was performed using 0.5 ml. of a dilution of sera from a control or drug treated group, 0.2 ml. of $2.5 \times 10^5$ labeled El$_4$ cells, and 0.3 ml. of a 1/40 dilution of rabbit complement previously absorbed with El$_4$ cells. The dilution giving 50% of maximal lysis of El$_4$ cells was determined from a linearized plot of dilution-versus percent lysis and was taken as the titer of the sera. Drug effects are computed as percent inhibition of the control antibody titer. The immunosuppressant activity for compounds of this invention was usually examined by determining relative inhibition of the cellular and humoral immune response at a daily oral dose of 10 mg/kg. Results of this testing effort are recorded in Table I.

A number of compounds of the present invention were studied in more depth, using the same El$_4$ test procedures described above. Activity was measured for each compound so that generally three points could be used to determine a dose-response line from which an ED$_{50}$ was calculated, i.e., the dose at which there was 50% inhibition of the immune response. Table II records the ED$_{50}$'s for inhibition of both the cellular and humoral immune response for these compounds.

TABLE I

Immunological Activity of [1]Benzothiopyrano[4,3-c]pyrazole-3-ones

| Structure | R | n | X | % Suppression of the Response to El$_4$ Cells(a) | |
|---|---|---|---|---|---|
| | | | | Cellular | Humoral |
| I | 4-ClC$_6$H$_4$ | 0 | H | >90 | >90 |
| I | C$_6$H$_5$ | 0 | H | 1 | (b) |
| I | 4-BrC$_6$H$_5$ | 0 | H | 84 | >90 |
| I | 4-FC$_6$H$_4$ | 0 | H | 86 | >90 |
| I | 2-ClC$_6$H$_4$ | 0 | H | 8 | 45 |
| I | 3-ClC$_6$H$_4$ | 0 | H | 16 | 67 |
| I | 4-CH$_3$C$_6$H$_4$ | 0 | H | 19 | 46 |
| I | 4-CH$_3$OC$_6$H$_4$ | 0 | H | −11 | −6 |
| I | 3,4-Cl$_2$C$_6$H$_3$ | 0 | H | 62 | 87 |
| I | 2,3-Cl$_2$C$_6$H$_3$ | 0 | H | 5 | 51 |
| I | 2,4-Cl$_2$C$_6$H$_3$ | 0 | H | −4 | 20 |
| I | 2,6-Cl$_2$C$_6$H$_3$ | 0 | H | 1 | 4 |
| I | 3,5-Cl$_2$C$_6$H$_3$ | 0 | H | 19 | 73 |
| I | 4-CF$_3$C$_6$H$_4$ | 0 | H | 71 | >90 |
| I | 4-NO$_2$C$_6$H$_4$ | 0 | H | 27 | (b) |
| I | 4-ClC$_6$H$_4$ | 1 | H | >90 | >90 |
| I | 4-ClC$_6$H$_4$ | 2 | H | 75 | — |
| II | 4-ClC$_6$H$_4$ | 0 | H | 63 | >90 |
| I | C$_6$H$_5$ | 0 | Cl | −5(c) | 38(c) |
| I | 4-ClC$_6$H$_4$ | 0 | Cl | 9(c) | 36(c) |
| I | 4-BrC$_6$H$_4$ | 0 | Cl | 23(c) | 36(c) |

(a)Unless otherwise specified, dosage was 10 mg./kg., oral.
(b)Data for the humoral response for this compound were considered unreliable.
(c)Dosage for this compound was 33 mg./kg., intramuscular.

TABLE II

Immunological Activity of Benzothiopyrano[4,3-c]pyrazol-3-ones

| R | Dose (mg./kg., oral) to inhibit immune response to El$_4$ cells by 50% | | Inhibition of secondary response - adjuvant arthritis | |
|---|---|---|---|---|
| | Cellular | Humoral | Dose (mg./kg. oral) | % |
| 4-ClC$_6$H$_4$ | 2 | 0.5 | 10 | 40 |
| | | | 40 | 71 |
| 3,4-Cl$_2$C$_6$H$_3$ | 3.0 | 1.0 | 10 | 40 |
| | | | 20 | 54 |
| 4-BrC$_6$H$_4$ | 3.3 | 2.0 | 20 | 59 |
| 4-FC$_6$H$_4$ | 5.5 | 3.3 | 10 | 23 |
| 4-CF$_3$C$_6$H$_4$ | 6.5 | 6.0 | — | — |
| 3,5-Cl$_2$C$_6$H$_3$ | 31 | 8.0 | 20 | 49 |
| 3-ClC$_6$H$_4$ | 45 | 9.0 | 10 | 39 |
| | | | 20 | 52 |
| C$_6$H$_5$ | 130 | 70 | — | — |
| 4-CH$_3$OC$_6$H$_5$ | 240 | 150 | 10 | 46 |

The immunological activity of compounds of the present invention was further assessed by the rat adjuvant arthritis procedure, as described by D. W. Walz et al. [Ann. Rheum. Dis., 30, 303 (1971) and J. Pharm. Exp. Ther., 178, 223 (1971)]. This test reflects an immunologically mediated inflammatory reaction developed in response to the injection of complete Freund's adjuvant.

Adjuvant arthritis was produced by a single subcutaneous injection of 1 mg. of *Mycobacterium butyricum* suspended in 0.1 ml. of mineral oil into the right hindpaws of male Lewis rats. The initial paw volume ($V_i$) was measured on the day of adjuvant injection. The swelling ($V_f$-$V_i$) of the injected hindpaw (right) measured on the 4th day after the injection of the adjuvant was considered as the primary response and the increase in volume ($V_f$-$V_i$) of the uninjected hindpaw (left) measured on the 16th day constituted the secondary response. Drugs were dissolved in water (dilute sodium hydroxide added if necessary to ensure solution) and administered orally in volume of 10 ml./kg. body weight by intubation with a blunt-end 18-gauge needle once daily for 17 days beginning on the day before the adjuvant injection. Results, expressed as percent suppression of the control, are shown in Table II.

As previously indicated, the benzothiopyrano[4,3-c]pyrazoles of the present invention are all readily adapted to therapeutic use as immunosuppressive agents in view of their ability to suppress antibody production and cell-mediated immunity. This type of activity is also exhibited by agents such as azathioprine and cyclophosphamide; such compounds have been shown to be of benefit in the treatment of rheumatoid arthritis, system lupus erythematosis, other autoimmune disorders and organ transplantation. The benzothiopyrano[4,3-c]pyrazoles of the present invention exhibit remarkable inhibitory activity in the mouse model of immunity described above. The most active 2-(4'-chlorophenyl)-1,2,3,4-tetrahydro-[1]benzothiopyrano(4,3-c)pyrazol-3-one (Ia) is effective at an oral dose of less than 1 mg./kg. and is five times more potent than cyclophoshamide and six times more potent than azathioprine as an immunosuppressant. More specifically, compound Ia exhibits activity in mice when tested orally at levels ranging from 0.5 to 100 mg./kg. This activity was not accompanied by lethality since the oral LD$_{50}$ in mice was found to be >400 mg./kg., p.o. and compound Ia was tolerated on chronic administration to the same species for 14 days with no bone marrow depression, no loss of cellularity in the spleen or thymus, and no abnormal pathology at oral doses up to 400 mg./kg. These data should be contrasted with results for cyclophosphamide and azathioprine in BALB/c mice where the oral ED$_{50}$ for inhibition of the cellular immune response to El$_4$ cells is 8 and 30 mg./kg. respectively, and the chronic oral LD$_{50}$ obtained after 14 days dosing (ca. 90 and ca. 125 mg./kg., respectively) differ by a factor of 10 and 4, respectively. For compound (Ia), the ED$_{50}$ and LD$_{50}$ differ by a factor of greater than 400. With both cyclophosphamide and azathioprine, depressive effects on spleen cellularity are readily noted at therapeutic doses. In addition, cyclophosphamide and azathioprine are both known mutagenic agents [McCann et al., Proc. Nat. Acad. Sci., 72, 3190 (1975); Speck and Rosenkranz, Cancer Res. 36, 108 (1976)]. In a system similar to that used to demonstrate the mutagenicity of cyclophosphamide, e.g., the number of revertants to histidine independence for several *Salmonella typhimurium* strains, compound (Ia) was found to lack mutagenic potential. Also in contrast to azathioprine and cyclophosphamide [see for example Tolchin et al., Arth. Rheum. 17, 375 (1974)], doses of Ia up to 300 mg./kg., p.o., did not cause chromosomal breakage in mouse bone marrow.

2-(4'-chlorophenyl)-1,2,3,4-tetrahydro-[1]benzothiopyrano[4,3-c]pyrazol-3-one showed no lethal effects when administered even at multiple high doses to mice, rats, hamsters and dogs. However, the compound was lethal to rabbits. Rats survived multiple doses of the compound but, like rabbits, exhibited some vacuolization of hepatocytes and focal areas of liver necrosis.

As stated above, the compounds of the present invention are immunosuppressant agents useful for inhibition of the immune mediated rejection of organ transplants, as well as for the therapy of autoimmune diseases. In order to use the compounds of this invention, they may be combined with inert pharmaceutical excipients such as lactose, mannitol and starch, and formulated into dosage forms such as tablets, capsules and the like. For parenteral administration, these compounds may be formulated with an inert, pharmaceutically-acceptable vehicle such as water, saline, sesame oil and the like. These various pharmaceutical dosage forms are compounded by methods well known to the pharmacist's art.

Variations in dosage may be made to achieve effective results which may depend on the subject being treated and individual response to the medicament, the weight of the subject as well as the particular type of compound formulation chosen and the time period and intervals at which such administration is conducted. In general, it will be found that an immunoregulating amount of the compounds of this invention ranges from 25 to 750 mg. per day, preferably 50 to 250 mg. per day. These amounts may be administered in single or multiple doses. In some instances, dosage levels below the lower limit of aforesaid range may be more than adequate while in other cases still larger doses may be employed without causing any harmful or deleterious side effects to occur provided that such higher dose levels are first divided into several smaller doses that are to be administered throughout the day.

The present invention is illustrated by the following examples. However, it should be understood that the invention is not limited to the specific details of these examples.

EXAMPLE 1

2-(4-Chlorophenyl)-1,2,3,4-tetrahydro-[1]benzothiopyrano[4,3-c]pyrazol-3-one

4Oxo-3-thiochromancarboxylic acid methyl ester (10.4 g., 0.047 mole), [prepared by the method of Moriwake, J. Med. Chem. 9, 163 (1966)], was added to a round bottom flask containing p-chlorophenylhydrazine (7.4 g., 0.052 mole) and 3 ml. of glacial acetic acid. After stirring to obtain a homogeneous mixture, the reaction mixture was heated under nitrogen at an oil bath temperature of 115° C. The reaction mixture quickly liquefied and then turned to a yellow solid. Heating was continued at 115° C. for 20 minutes and the temperature then gradually raised to 180° C. and maintained there for about an hour. The reaction mixture was then cooled to room temperature, the solid was collected by filtration, washed with ether and dried. Recrystallization from isopropanol afforded product, m.p. 235° to 237° C. Weight: 10.3 g (70%).

Analysis: Calcd. for $C_{16}H_{11}N_2OSCl$; C, 61.04; H, 3.52; N, 8.90.

Found: C, 61.04; H, 3.65; N, 8.79.

EXAMPLE 2

2-(4-Chlorophenyl)-1,2,3,4-tetrahydro[1]benzothiopyrano[4,3-c]pyrazol-3-one-5-oxide In a 50 ml. round bottom flask under nitrogen was placed 2-(p-chlorophenyl)-1,2,3,4-tetrahydro[1]benzothiopyrano[4,3-c]pyrazole-3-one (0.5 g., 0.0016 mole) 8.33 ml. of glacial acetic acid and 3 ml. of 30% hydrogen peroxide. After stirring at 0° C., for 3.5 hours, the resulting solid was removed by filtration, washed with glacial acetic acid and dried in vacuo over phosphorous pentoxide to afford product, m.p. 193° C. (dec.). Weight 0.42 g. (80%). A second crop (0.4 g., 8%) was obtained from mother liquors.

Analysis: Calcd. for $C_{16}H_{11}O_2N_2SCl$: C, 58.09; H, 3.35; N, 8.47.

Found: C, 58.38; H, 3.22; N, 8.16.

EXAMPLE 3

2-(p-Chlorophenyl)-1,2,3,4-tetrahydro[1]benzothiopyrano[4,3-c]pyrazol-3-one-5,5-dioxide In a 65 ml. round bottom flask was placed 2-(p-chlorophenyl)-1,2,3,4-tetrahydro-[1]benzothiopyrano[4,3-c]pyrazol-3-one (1.0 g., 0.008 mole) in 15 ml. of glacial acetic acid. To this solution at 0° C. was added dropwise 1.5 ml. of 30% hydrogen peroxide. The resultant yellow-white suspension was allowed to come to room temperature and the stirring was continued for 16 hours. Excess peroxide was quenched with a saturated solution of sodium bisulfate. The resultant yellow solid was filtered and dried in vacuo over pentoxide to afford crude product. The crude solid was partitioned between benzene and water. The solid in the benzene phase was removed by filtration and dried in vacuo to yield the desired product, m.p. 220° C. (dec.).

Analysis: Calcd. for $C_{16}H_{11}O_3N_2SCl$: C, 55.41; H, 3.17; N, 8.08.

Found: C, 55.41; H, 3.23; N, 8.05.

EXAMPLE 4 p-Chlorothiophenoxypropionic Acid

In a 5 liter 3-neck round bottom flask was placed p-chlorobenzenethiol (144.5 g., 1 mole) in 340 ml. of 3 N KOH and the mixture was stirred at room temperature under a nitrogen atmosphere. In a separate flask 3-chloropropionic acid (108.5 g., 1 mole) was dissolved in 150 ml. of water and placed in a dropping funnel. In another dropping funnel was placed 325 ml. of 3 N KOH. Both solutions were added dropwise over a period of about an hour to the p-chlorobenzenthiol.

The resultant dark brown solution was heated to reflux for 25 minutes. The reaction mixture was cooled to 5° C. and a liter of water was added. The temperature was maintained at 5° C. as concentrated HCl was added to the reaction mixture until it was acidic. The resultant white solid was removed by filtration, washed with 1.5 liters of water and then dissolved in 1.5 liters of ethyl acetate. The ethyl acetate solution was washed with water (2×750 ml.) and then with saturated sodium chloride solution (2×500 ml.). The ethyl acetate solution was dried over sodium sulfate and then distilled in vacuo. The resultant yellow solid was dissolved in 1000 ml. of cyclohexane. This solution was reduced to 500 ml. by heating and then cooled. Crystalline solid formed which was removed by filtration and dried in vacuo to afford product, m.p. 89° to 91° C. Weight: 180.5 g. (83.4%).

Analysis: Calcd for $C_9H_9O_2SCl$: C, 49.89; H, 4.19. Found: C, 49.74; H, 4.30.

6-Chlorothiochroman-4-one

In a 3 liter 3-neck round bottom flask was placed 815.6 grams of polyphosphoric acid which was heated to 80° C. with stirring under nitrogen. To the flask was added portion-wise p-chlorothiophenoxypropionic acid (90 g., 0.416 mole). The red viscous liquid was stirred at 80° C. for about 3.5 hours. The reaction mixture was poured into 2 liters of ice water and stirred for 30 minutes in an ice bath. The yellow solid was removed by filtration and dried in vacuo over phosphorous pentoxide to afford product, m.p. 69°–71° C. Weight: 43.9 g. (53.2%).

Analysis: Calcd for $C_9H_7OSCl$: C, 54.41; H, 3.55. Found: C, 54.55; H, 3.58.

Methyl 6-Chloro-4-oxothiochroman-3-glyoxyate

In a 3 liter 3-neck round bottom flask fitted with a mechanical stirrer and condenser was placed dimethyl oxalate (167.9 g. 1.423 moles), fresh sodium methylate (76.8 g., 1.423 moles) and 1.2 liters of anhydrous benzene. The resultant white suspension was refluxed for about 20 minutes and then cooled to 10° C. A clear red-brown solution of 6-chloro-4-thiochromanone (131 g., 0.662 moles) in 800 ml. of benzene was added dropwise while maintaining the reaction temperature below 10° C. The dark red-brown mixture was stirred overnight at room temperature and subsequently poured into a liter of water. Then 41.2 ml. of 1 N KOH was added and the layers separated. The benzene layer was again extracted with 0.3 N KOH (4×500 ml.). The combined alkaline solutions were cooled and 3 N HCl was added until the pH was 4. The resultant solid was filtered and dried at 60° C. under vacuum to give product, m.p. 101°–105° C.

Analysis: Calcd for $C_{12}H_9O_4SCl$: C, 50.62; H, 3.19. Found: C, 50.62; H, 2.97.

Methyl 6-Chloro-4-oxothiochroman-3-carboxylate

Methyl 6-chloro-4-oxothiochroman-3-glyoxylate (10.1 g., 0.0352 mole) was mixed with 5 grams of powdered glass and heated in an oil bath for one hour at 180° C. The reaction mixture was cooled to 0° C., acetone was added and the powdered glass removed by filtration. The acetone filtrate was concentrated in vacuo. The resultant brown solid was dried in vacuo over phosphorous pentoxide to give crude product, m.p. 64°–67° C. Weight 7.4 g. (81.8%). Recrystallization from methanol afforded analytically pure product, m.p. 81°–83° C.

Analysis: Calcd for $C_{11}H_9O_3SCl$: C, 51.46; H, 3.53; N, 12.49. Found: C, 51.84; H, 3.59; N, 12.62.

8-Chloro-2-phenyl-1,2,3,4-tetrahydro[1]benzothiopyrano[4,3-c]pyrazol-3-one

In a 50 ml. round bottom flask was placed methyl 6-chloro-4-oxothiochroman-3-carboxylate (2.0 g., 0.0078 mole), phenylhydrazine (0.93 g., 0.0086 mole) and 0.5 ml. of acetic acid. The reaction mixture was heated under nitrogen at an oil bath temperature of 115° C. for 30 minutes and then at 180° C. for 2.5 hours. The reaction mixture was cooled to room temperature and the acetic acid was removed in vacuo. The residue was triturated with ether and yellow solid removed by filtration and dried in vacuo over phosphorous pentoxide to give product, m.p. 212°–216° C. Weight: 2.03 g. (82.5%).

Analysis: Calcd for $C_{16}H_{11}ON_2SCl$: C, 61.04; H, 3.52; N, 8.90. Found: C, 60.60; H, 3.80; N, 8.67.

By the same procedure methyl 6-chloro-4-oxothiochroman-3-carboxylate was reacted with 4-chlorophenylhydrazine and 4-bromophenylhydrazine to yield 8-chloro-2-(4-chlorophenyl)-1,2,3,4-tetrahydro[1]benzothiopyrano[4,3-c]pyrazol-3-one (m.p. 237°–240° C.) and 8-chloro-2-(4-bromophenyl)-1,2,3,4-tetrahydro[1]benzothiopyrano[4,3-c]pyrazol-3-one (m.p. 257°–260° C.), respectively.

EXAMPLE 5

2-(4-Chlorophenyl-2,3-dihydro[1]benzothiopyrano[4,3-c]pyrazol-3-one

Method A

To a solution of 2-(4-chlorophenyl)-1,2,3,4-tetrahydro[1]benzothiopyrano[4,3-c]pyrazol-3-one (2.0 g., 0.0063 mole) in 20 ml of DMSO was added o-chloranil (1.55 g. 0.0063 mole). An orange precipitate appeared immediately and became heavier upon stirring the reaction at room temperature. After 1.5 hour, the solid was filtered, rinsed with cold benzene and dried in vacuo to yield 1.68 g. (84%) of product, m.p. 220°–231° C.

Analysis: Calcd for $C_{16}H_9N_2OSCl$: C, 61.44; H, 2.90; N, 8.96. Found: C, 61.09; H, 3.24; N, 8.69.

Method B

To 2-(4-chlorophenyl)-1,2,3,4-tetrahydro[1]benzothiopyrano[4,3-c]pyrazol-3-one-5-oxide (0.050 g., 0.00015 mole) in 5 ml. of HOAc was added 5 drops of 12 N HCl. The suspension rapidily cleared to a yellow solution and, after 3.5 hours at 85° C., was completely converted (TLC evidence, 85:15, benzene/HOAc, as eluent) to a new, less polar, visible yellow spot on TLC. Upon cooling of the reaction, an orange solid precipitated. The solid was filtered and dried to yield 0.030 g. (64%) of product, m.p. 231°–232° C., identical by ir, mass spectrum and combustion analysis to the material isolated from Method A.

EXAMPLE 6

The method of Example 5, Method A was repeated with 2-phenyl-1,2,3,4-tetrahydro-[1]benzothiopyran[4,3-c]pyrazol-3-one to yield the dihydrate of 2-phenyl-3-oxo-2,3-dihydro-[1]benzothiopyrano[4,3-c]pyrazole, m.p. 160° C. (dec.).

EXAMPLE 7

Methyl 4-oxo-3-thiochromancarboxylate and appropriate hydrazines were reacted by the method of Example 1 to yield [1]benzothiopyrano[4,3-c]pyrazole-3-ones of the formula

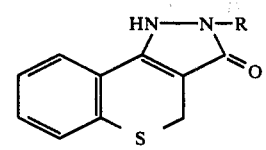

| R | X | Yield % | Reaction Time, hrs. | Reaction Temp., °C. | m.p. (°C.) | Crystn. Solvent[a] |
|---|---|---|---|---|---|---|
| $C_6H_5$ | H | 48 | 1 | 115 | 208–210 | I |
| 4-$BrC_6H_4$ | H | 23 | 2 | 115 | 239–241 | I |
| 4-$CH_3C_6H_4$ | H | 44 | 2 | 115 | 239–241 | Et |
| 4-$CH_3OC_6H_4$ | H | 35 | 2 | 130 | 175–179 | E |
| 3,4-$Cl_2C_6H_3$ | H | 30 | 2 | 115 | 219–221 | I |
| 4-$NO_2C_6H_4$ | H | 10 | 6 | 130 | 246–dec. | C-M |
| 4-$FC_6H_4$ | H | 48 | 10 | 150 | 193–196 | Et |
| 3-$ClC_6H_4$ | H | 50 | 30 | 180 | 202–204 | Et |
| 2-$ClC_6H_4$ | H | 34[b] | 12 | 180 | 233–235 | B |
| 2,3-$Cl_2C_6H_3$ | H | 39[b] | 12 | 180 | 228–230 | Et |
| 2,4-$Cl_2C_6H_3$ | H | 54 | 35 | 180 | 274–276 | Et |
| 3,5-$Cl_2C_6H_3$ | H | 42 | 22 | 180 | 245–247 | Et |
| 4-$CF_3C_6H_4$ | H | 14 | 4 | 180 | 282–284 | I |

[a] I = isopropanol; Et = thorough trituration with ether; E = ethanol; C-M = chloroform-methanol; B = benzene.

[b] To complete these reactions, an additional 0.25–0.50 equiv. of the hydrazine was required.

EXAMPLE 8

The 1,2,3,4-tetrahydro[1]benzothiopyrano[4,3-c]pyrazol-3-ones of Example 7 are oxidized to the corresponding 2,3-dihydro compounds by the method of Example 5.

EXAMPLE 9

The 1,2,3,4-tetrahydro[1]benzothiopyrano[4,3-c]pyrazol-3-ones of Example 7 are oxidized to the corresponding 5-oxides and 5,5-dioxides by the methods of Examples 2 and 3.

We claim:

1. A compound of structure:

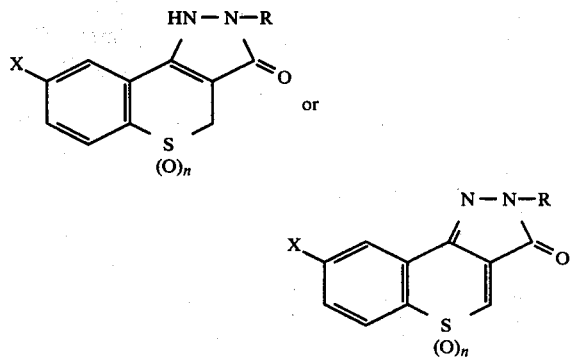

wherein n is an integer of value from 0 to 2;

R is phenyl; phenyl monosubstituted with chloro, bromo, fluoro, methyl, methoxy, nitro or trifluoromethyl; or phenyl disubstituted with chloro in other than 2,6-position; and X is hydrogen or chloro.

2. A compound of claim 1 wherein X is hydrogen and R is phenyl mono-substituted in the 4-position with chloro, bromo or fluoro.

3. 2-(4-Chlorophenyl)-1,2,3,4-tetrahydro[1]benzothiopyrano[4,3-c]pyrazol-3-one.

4. 2-(4-Bromophenyl)-1,2,3,4-tetrahydro[1]benzothiopyrano[4,3-c]pyrazol-3-one.

5. 2-(4-Fluorophenyl)-1,2,3,4-tetrahydro[1]benzothiopyrano[4,3-c]pyrazol-3-one.

6. 2-(4-Chlorophenyl)-1,2,3,4-tetrahydro[1]benzothiopyrano[4,3-c]pyrazol-3-one-5-oxide.

7. 2-(4-Chlorophenyl)-1,2,3,4-tetrahydro[1]benzothiopyrano[4,3-c]pyrazol-3-one-5,5-dioxide.

8. 2-(4-Chlorophenyl)-2,3-dihydro[1]benzothiopyrano[4,3-c]pyrazol-3-one.

9. A compound of claim 1 wherein X is hydrogen and R is phenyl disubstituted in the 3,4- or 3,5-position with chloro.

10. 2-(3,4-Dichlorophenyl)-1,2,3,4-tetrahydro[1]benzothiopyrano[4,3-c]pyrazol-3-one.

11. A pharmaceutical composition suitable for oral or parenteral administration in suppressing body immune responses comprising a pharmaceutically-acceptable carrier and an immune suppressing amount of a compound of claim 1.

12. A pharmaceutical composition of claim 11 wherein the compound is 2-(4-chlorophenyl)-1,2,3,4-tetrahydro[1]benzothiopyrano[4,3-c]pyrazol-3-one.

13. A pharmaceutical composition of claim 11 wherein the compound is 2-(4-bromophenyl)-1,2,3,4-tetrahydro[1]benzothiopyrano[4,3-c]pyrazol-3-one.

14. A pharmaceutical composition of claim 11 wherein the compound is 2-(4-fluorophenyl)-1,2,3,4-tetrahydro[1]benzothiopyrano[4,3-c]pyrazol-3-one.

15. A pharmaceutical composition of claim 11 wherein the compound is 2-(4-chlorophenyl)-2,3-dihydro[1]benzothiopyrano[4,3-c]pyrazol-3-one.

16. A pharmaceutical composition of claim 11 wherein the compound is 2-(3,4-dichlorophenyl)-1,2,3,4-tetrahydro[1]benzothiopyrano[4,3-c]pyrazol-3-one.

17. A method of suppressing body immune responses in a mammal, other than a rabbit, in need of such treatment comprising orally or parenterally administering a body immune suppressing amount of a compound of claim 1 to said mammal.

18. A method of claim 17 wherein the compound is 2-(4-chlorophenyl)-1,2,3,4-tetrahydro[1]benzothiopyrano[4,3-c]pyrazol-3-one.

19. A method of claim 17 wherein the compound is 2-(4-bromophenyl)-1,2,3,4-tetrahydro[1]benzothiopyrano[4,3-c]pyrazol-3-one.

20. A method of claim 17 wherein the compound is 2-(4-fluorophenyl)-1,2,3,4-tetrahydro[1]benzothiopyrano[4,3-c]pyrazol-3-one.

21. A method of claim 17 wherein the compound is 2-(4-chlorophenyl)-2,3-dihydro[1]benzothiopyrano[4,3-c]pyrazol-3-one.

22. A method of claim 17 wherein the compound is 2-(3,4-dichlorophenyl)-1,2,3,4-tetrahydro[1]benzothiopyrano[4,3-c]pyrazol-3-one.

* * * * *